US008455414B2

(12) United States Patent
Sabahi et al.

(10) Patent No.: US 8,455,414 B2
(45) Date of Patent: Jun. 4, 2013

(54) MACROMOLECULAR AMINE-PHENOLIC ANTIOXIDANT COMPOSITIONS, PROCESS TECHNOLOGY THEREOF, AND USES THEREOF

(75) Inventors: Mahmood Sabahi, Baton Rouge, LA (US); Vincent J. Gatto, Baton Rouge, LA (US); Hassan Y. Elnagar, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 1050 days.

(21) Appl. No.: 12/444,183

(22) PCT Filed: Oct. 17, 2007

(86) PCT No.: PCT/US2007/081604
§ 371 (c)(1),
(2), (4) Date: Apr. 3, 2009

(87) PCT Pub. No.: WO2008/048989
PCT Pub. Date: Apr. 24, 2008

(65) Prior Publication Data
US 2012/0115764 A1    May 10, 2012

Related U.S. Application Data

(60) Provisional application No. 60/829,838, filed on Oct. 17, 2006.

(51) Int. Cl.
*C10L 1/183*    (2006.01)
(52) U.S. Cl.
USPC ............ 508/560; 568/722; 568/723; 564/315
(58) Field of Classification Search
None
See application file for complete search history.

(56) References Cited

U.S. PATENT DOCUMENTS

| 2,528,769 | A | 11/1950 | McCracken |
| 3,673,091 | A | 6/1972 | Werzner et al. |
| 3,812,152 | A | 5/1974 | Hofer et al. |
| 3,822,284 | A | 7/1974 | Werner et al. |
| 3,989,738 | A | 11/1976 | Kline |
| 4,994,628 | A | 2/1991 | Goddard et al. |

FOREIGN PATENT DOCUMENTS

| EP | 0269981 A | 6/1988 |
| EP | 0330613 A2 | 8/1989 |
| JP | 05331149 A | 12/1993 |
| SU | 572457 A1 | 9/1977 |

OTHER PUBLICATIONS

Decodts, Guy; "Alkylation of Indoles With Halomethylphenols. III. Mechanism of the Rearrangement of 3H-3-(P-Hydroxybenzyl) Indoles to 1H-1-(P-Hydroxybenzyl Indoles"; Bulletin De La Societe Chimique De France. 1 Partie—Chimie Analytique, Minerale Et Physique, Societe Francaise De Chimie. Paris, FR, 1976, pp. 1839-1840, XP008078012.

Mukmeneva, N.A., et al; "Inhibiting Properties of Substituted Arylamines With 3,5-di-tert-butyl-4-hydroxybenzyl Fragment"; Aging of Polymers, Polymer Blends and Polymer Composites, 2, 197-203 CODEN: APPBCH, 2002, XP008077915.

Dinoiu, Vasile, et al; "Synthesis and ESR Spectra of Persistent Aroxyls. Part 6. 1-(3,5-Dialkyl-4-hydroxybenzyl)-pyrazole and -pyrazol-5-one Derivatives, and Their Corresponding Aroxyls"; Revue Roumaine De Chimie, 39(8), 949-54, CODEN: RRCHAX; ISSN: 0035-3930, 1994; XP008077988.

Herdan, Jean, et al; "4-Substituted 2,6-di-tert-butylphenols and Their Corresponding Aroxyls Possessing 4-(1-methyleneimidazolyl), 4-(1-methylenebenzimidazolyl), or 4-(1-sulfonylbenzimidazotyl) Groups"; Revue Roumaine De Chimie, 28(2), 129-37; CODEN: RRCHAX; ISSN: 0035-3930, 1983, XP008077976.

Bukharov, Sergey V., et al; "Purposeful Synthesis of Stabiliiers with Sterically Hindered Hydroxybenzyl Fragments and the Prospects for their Practical Use"; Materiely Yubileinoi Nauchno-Metodicheskoi Konferentsii "III Kirpichnikovskie Chteniya", Kazan, Russian Federation Mar. 25-28, 2003, 97-100. Editor(s): Mukmeneva, N.A. Publisher: Kazanskii Gosudarstvennyi Tekhnologicheskii Universitet; Kazan; RUS, 2003, XP008077914.

Decodts, Guy; et al "Alkylation of Indoles with Hydroxymethyl-, Aminomethyl-, and (halomethyl)phenols"; Tetrahedron; 26(13), 3313-28; CODEN TETRAB; ISSN:0040-4020, 1970, XP002430528.

*Primary Examiner* — Brian J Davis
(74) *Attorney, Agent, or Firm* — James A. Jubinsky

(57) ABSTRACT

This invention relates to novel macromolecular amine-phenolic compositions having oxidation inhibition characteristics that are exhibited when added to organic material normally susceptible to oxidative degradation in the presence of air or oxygen, such as petroleum products, synthetic polymers, and elastomeric substances.

8 Claims, No Drawings

MACROMOLECULAR AMINE-PHENOLIC ANTIOXIDANT COMPOSITIONS, PROCESS TECHNOLOGY THEREOF, AND USES THEREOF

REFERENCE TO RELATED APPLICATION

This application is the National Stage of International Patent Appl. No. PCT/US2007/081604, filed on Oct. 17, 2007, which claims priority on U.S. Provisional Application No. 60/829,838 filed on Oct. 17, 2006, the disclosures of which are incorporated herein by reference.

FIELD OF THE INVENTION

This invention relates to novel macromolecular amine-phenolic compositions having oxidation inhibition characteristics that are exhibited when added to organic materials normally susceptible to oxidative degradation in the presence of air or oxygen, such as petroleum products, synthetic polymers, and elastomeric substances.

BACKGROUND OF THE INVENTION

It is well known that a wide variety of organic materials are susceptible to oxidative degradation in the presence of air or oxygen, especially when at elevated temperatures. Such organic materials include, for example, gasolines, diesel fuels, burner fuels, gas turbine and jet fuels, automatic transmission fluids, gear oils, engine lubricating oils, thermoplastic polymers, natural and synthetic rubber, and the like. Over the years, considerable efforts have been devoted to discovery and development of compounds capable of minimizing the degradation of one or more of such materials. As conditions of use and exposure of such materials to various oxygen containing environments change over the years, the desire for new effective macromolecular oxidation inhibitors (a.k.a. antioxidants) continues. Also, the art benefits greatly if new and highly effective process technology is provided for producing known effective macromolecular oxidation inhibitors.

U.S. Pat. No. 3,673,091 discloses forming oxidation inhibitors by the reaction between 3,5-di-tert-butyl-4-hydroxybenzyl alcohol and aryl amines, carbazole, phenazines, or acridines. Unfortunately, the resultant reaction product is a complex mixture containing large quantities of unreacted amine starting material and in which the desired products are formed in low yields.

SUMMARY OF THE INVENTION

In some embodiments, the present invention relates to macromolecular antioxidant products having properties enhancing their usefulness as oxidation inhibitors, especially for petroleum products of the types referred to above. These macromolecular reaction product typically comprise one or more i) aromatic amines substituted with one 3,5-di-hydrocarbyl-4-hydroxylbenzyl groups; ii) aromatic amines substituted with two 3,5-di-hydrocarbyl-4-hydroxylbenzyl groups; iii) aromatic amines substituted with three 3,5-di-hydrocarbyl-4-hydroxylbenzyl groups; iv) aromatic amines substituted with four 3,5-di-hydrocarbyl-4-hydroxylbenzyl groups; v) aromatic amines substituted with five 3,5-di-hydrocarbyl-4-hydroxylbenzyl groups; vi) aromatic amines substituted with six 3,5-di-hydrocarbyl-4-hydroxylbenzyl groups; and vii) one or more methylene-bridged aromatic amines substituted with one or more 3,5-di-hydrocarbyl-4-hydroxylbenzyl groups. The macromolecular antioxidant products are liquid at room temperatures or solids that melt at less than about 100° C. and are capable of being dissolved in liquid hydrocarbon solvents.

Preferred macromolecular antioxidant products of the present invention are compounds that are liquid at room temperatures (about 23° C.) or solids that melt at less than about 100° C., preferably about 60° C., and that are capable of being dissolved in common organic solvents and especially in liquid hydrocarbon solvents. In addition, in many cases these products have higher solubility in lubricants such as, for example, a base oil consisting of 50% by volume of high viscosity index 100 Neutral and 50% by volume of high viscosity index 250 Neutral such as referred to in U.S. Pat. No. 3,673,091.

Still another aspect of this invention is the provision of new antioxidant formulations especially adapted for use in lubricating oils, and especially in lubricating oils for internal combustion engines. These and other antioxidant formulations are also described in detail hereinafter.

The above and other aspects, features, and embodiments of this invention will be s further apparent from the ensuing description and appended claims.

DETAILED DESCRIPTION OF THE INVENTION

Products of the Invention

As noted above, the macromolecular reaction products of the present invention are useful as antioxidants; thus, these macromolecular phenol-aromatic amine reaction products are sometimes referred to herein as alkylated aromatic amines, antioxidant products, macromolecular antioxidant compositions, or macromolecular oxidation inhibitors for simplicity. As stated above, preferred antioxidant products of the present invention are compounds that are liquid at room temperatures (about 23° C.) or solids that melt at less than about 100° C., preferably about 60° C., and that are capable of being dissolved in common organic solvents and especially in liquid hydrocarbon solvents. In addition, in many cases these products have higher solubility in lubricants such as, for example, a base oil consisting of 50% by volume of high viscosity index 100 Neutral and 50% by volume of high viscosity index 250 Neutral such as referred to in U.S. Pat. No. 3,673,091.

The antioxidant products of the present invention typically comprise one or more alkylated aromatic amines, and one or more alkylated aromatic amines having one or more methylene bridge(s). The alkylated aromatic amines typically comprise one or more i) aromatic amines substituted with one 3,5-di-hydrocarbyl-4-hydroxylbenzyl groups, sometimes referred to herein as mono-alkylated aromatic amines; ii) aromatic amines substituted with two 3,5-di-hydrocarbyl-4-hydroxylbenzyl groups, sometimes referred to herein as di-alkylated aromatic amines; iii) aromatic amines substituted with three 3,5-di-hydrocarbyl-4-hydroxylbenzyl groups, sometimes referred to herein as tri-alkylated aromatic amines; iv) aromatic amines substituted with four 3,5-di-hydrocarbyl-4-hydroxylbenzyl groups, sometimes referred to herein as tetra-alkylated aromatic amines; v) aromatic amines substituted with five 3,5-di-hydrocarbyl-4-hydroxyl-benzyl groups, sometimes referred to herein as penta-alkylated aromatic amines; vi) aromatic amines substituted with six 3,5-di-hydrocarbyl-4-hydroxylbenzyl groups, sometimes referred to herein as hexa-alkylated aromatic amines; and vii) one or more methylene-bridged aromatic amines substituted with one or more 3,5-di-hydrocarbyl-4-hydroxylbenzyl groups. It is preferred that the reaction products of the present invention contain less than about 5 wt. % of aromatic amines substituted with one 3,5-di-hydrocarbyl-4-hydroxylbenzyl groups, based on the total weight of the reaction product. In other embodiments the reaction products of the present invention contain 10 wt. % or less of aromatic amines substituted with two 3,5-di-hydrocarbyl-4-hydroxylbenzyl groups. In still other embodiments the antioxidant products of the present invention contain 5 wt. % or less of aromatic amines substituted with one 3,5-di-hydrocarbyl-4-hydroxylbenzyl groups and aromatic amines substituted with two 3,5-di-hydrocarbyl-4-hydroxylbenzyl groups, on the same basis. In some embodiments, the antioxidant products of the present invention comprise greater than 40 wt. %, in some embodiments greater than about 45 wt. %, in other embodiments, greater than about 50 wt. %, of aromatic amines substituted with four 3,5-di-hydrocarbyl-4-hydroxylbenzyl groups, aromatic amines substituted with five 3,5-di-hydrocarbyl-4-hydroxylbenzyl groups, or aromatic amines substituted with six 3,5-di-hydrocarbyl-4-hydroxylbenzyl groups, all based on the total weight of the antioxidant product. In the above embodiments, the antioxidant products of the present invention contain in the range of from about 1 to about 20 wt. %, preferably in the range of from about 1 to about 15 wt. %, and most preferably in the range of about 1 to 10 wt % of one or more methylene-bridged aromatic amines substituted with one or more 3,5-di-hydrocarbyl-4-hydroxylbenzyl groups, all based on the total weight of the antioxidant product.

In some embodiments, the antioxidant products of the present invention can be described as comprising i) less than about 5 wt. %; preferably less than about 1 wt. %, more preferably less than about 0.5 wt. %, aromatic amines substituted with one 3,5-di-hydrocarbyl-4-hydroxylbenzyl groups, all based on the total weight of the antioxidant product; ii) less than about 10 wt. %; preferably less than about 5 wt. %, more preferably less than about 1 wt. %, aromatic amines substituted with two 3,5-di-hydrocarbyl-4-hydroxylbenzyl groups, all based on the total weight of the antioxidant product; iii) in the range of from about 1 wt. % to about 35 wt. %, preferably in the range of from about 5 wt. % to about 25 wt. %, more preferably in the range of from about 5 wt % to about 20 wt. % aromatic amines substituted with three 3,5-di-hydrocarbyl-4-hydroxylbenzyl groups, on the same basis; iv) in the range of from about 10 wt % to about 65 wt. %, preferably in the range of from about 15 wt % to about 60 wt. %, more preferably in the range of from about 20 wt % to about 55 wt. % aromatic amines substituted with four 3,5-di-hydrocarbyl-4-hydroxylbenzyl groups, on the same basis; v) in the range of from about 5 wt % to about 60 wt. %, preferably in the range of from about 8 wt % to about 50 wt. %, more preferably in the range of from about 10 wt % to about 40 wt. % aromatic amines substituted with five 3,5-di-hydrocarbyl-4-hydroxyl-benzyl groups, on the same basis; vi) in the range of from about 1 wt % to about 50 wt. %, preferably in the range of from about 5 wt % to about 35 wt. %, more preferably in the range of from about 5 wt % to about 20 wt. % aromatic amines substituted with six 3,5-di-hydrocarbyl-4-hydroxylbenzyl groups, on the same basis; and vii) in the range of from about 1 to about 20 wt. %, preferably in the range of from about 1 to about 15 wt. %, more preferably in the range of from about 1 wt % to about 10 wt. % of one or more methylene-bridged aromatic amines substituted with one or more 3,5-di-hydrocarbyl-4-hydroxylbenzyl groups.

The antioxidant products of the present invention also contain in the range of from about 1 to about 10 wt. %, preferably in the range of from about 1 to about 5 wt. % of one or more phenolics represented by the following general formula:

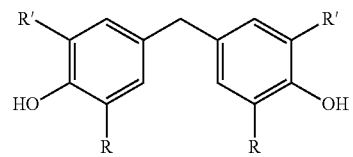

wherein each R and R' are independently H or a hydrocarbyl. In preferred embodiments, R and R' are H or a straight or branched chain, preferably branched chain, alkyl group. In a particularly preferred embodiment R and R' are tert-butyl and the compound is 4,4'-methylenebis(2,6-di-tert-butylphenol):

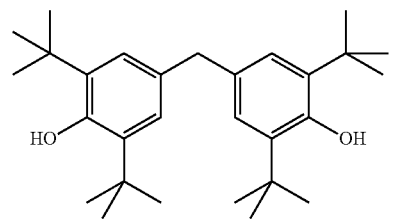 [SMILES: CC(C)(C)c1cc(Cc2cc(C(C)(C)C)c(O)c(C(C)(C)C)c2)cc(C(C)(C)C)c1O]

In some embodiments, the macromolecular antioxidant compositions of the present invention comprise one or more compounds that can be represented by the following general formula, Formula I:

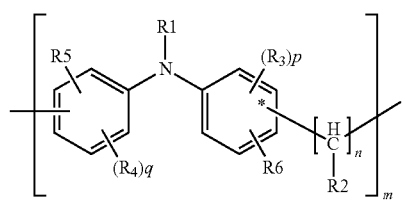

wherein $R_1$ is H or hydrocarbyl, $R_2$ is H, $R_3$ & $R_4$ are 3,5-dihydrocarbyl-4-hydroxybenzyl, $R_5$ and $R_6$ are H or hydrocarbyl, n is a whole number in the range of from about 0 to about 1, p and q are whole numbers and p+q is in the range of from 1 to 8, m is 1 when n=0 and in is a whole number in the range of from about 2 to about 10 when n=1. It should be noted that in some embodiments, the macromolecular antioxidant compositions of the present invention contain more than one molecule represented by the above-described general formula. In these embodiments, each of the one or more compounds can have the same or different constituents for $R_1$, $R_2$, $R_3$, $R_4$, $R_5$, and $R_6$ and each of the one or more compounds can have the same or different values for p, q, in, and n.

In some embodiments, the macromolecular antioxidant compositions of the present invention contain one or more, preferably two or more, compounds represented by the following general formula:

Formula II:

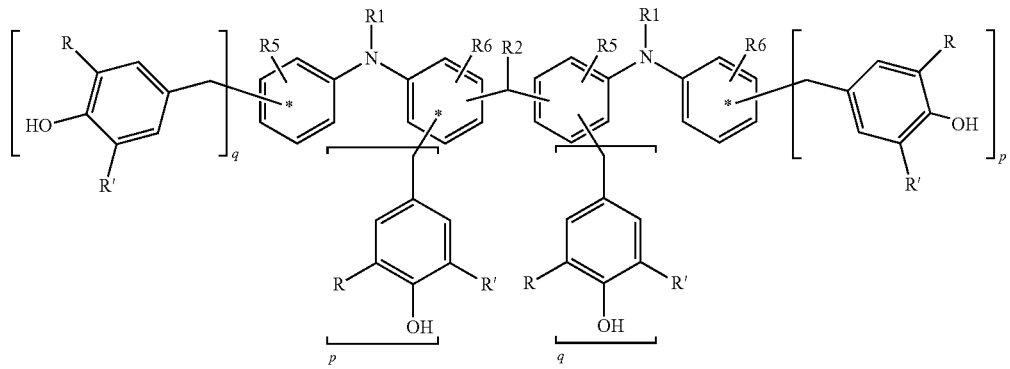

wherein $R_1$, $R_5$, and $R_6$ of Formula II are independently H or hydrocarbyl, $R_2$ is H, each R & R' are independently hydrogen or a branched or straight chain alkyl containing in the range of from about 1 to about 8 carbons, preferably in the range of from about 1 to about 4 carbon atoms, and p and q are independently whole numbers, wherein p+q is 6. It should be noted that if the macromolecular antioxidant compositions of the present invention contain more than one compound of Formula II, each of the compounds can have the same or different constituents for $R_1$, $R_2$, $R_5$, and $R_6$, R and R', and each of the one or more compounds can have the same or different values for p and q; and Formula III:

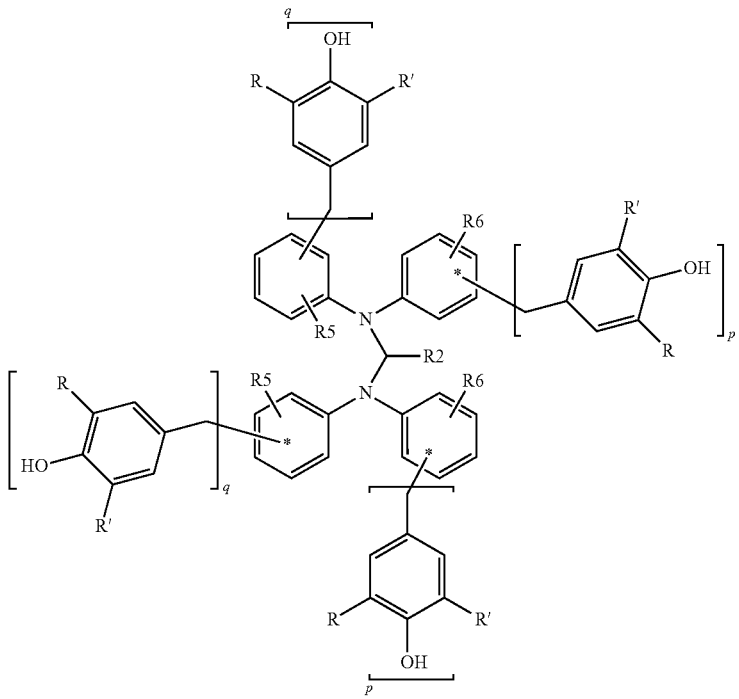

wherein $R_1$, $R_2$, $R_5$, $R_6$, R, R', are the same as described above, and p and q are whole numbers and p+q is in the range of from 1 to 8. It should be noted that if the macromolecular antioxidant compositions of the present invention contain more than one compound of Formula III, each of the compounds can have the same or different constituents for $R_1$, $R_2$, $R_5$, and $R_6$, R and R', and each of the one or more compounds can have the same or different values for p and q.

It is also obvious to those skilled in the art that the substitution pattern shown in Formulas I, II, and III is for visual representation only and the alkyl and phenolic substitutions may take place on all the available active sites on the amine molecule.

Some non-limiting examples of specific compounds represented by the above-described formulas are:

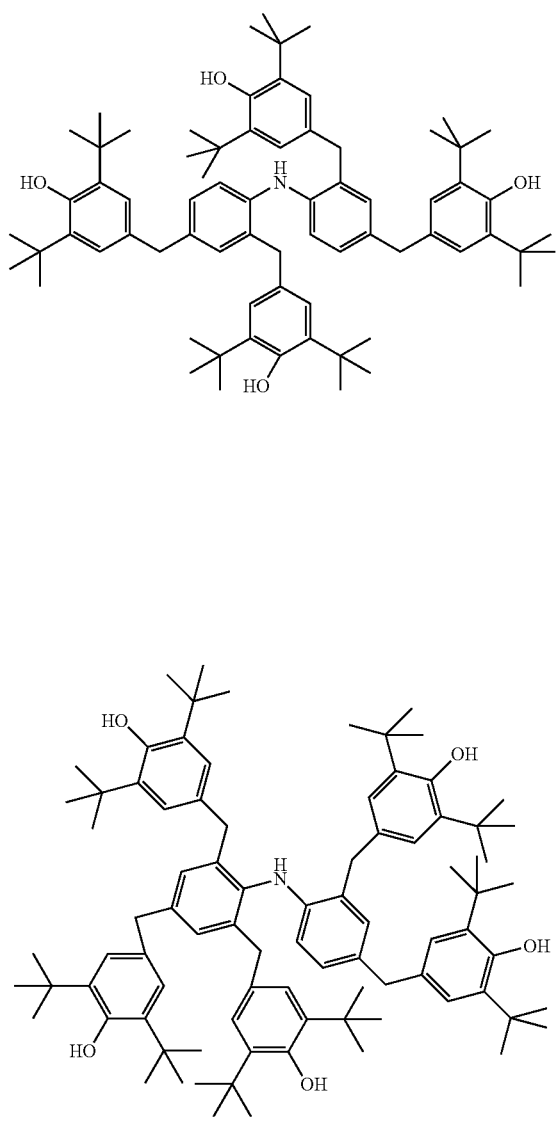

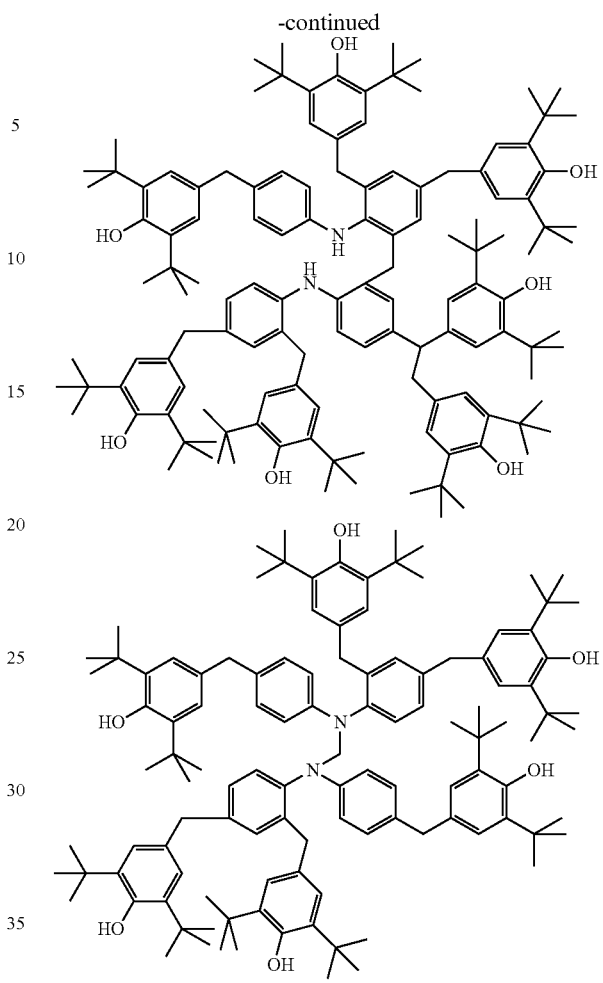

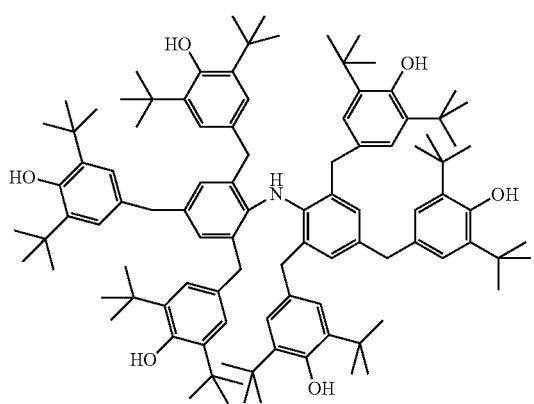

The antioxidant products of this invention, such as those described above, preferably have boiling points at atmospheric pressure of at least about 175° C. The number or average number of 2,6-dihydrocarbyl-4-hydroxybenzyl groups in the products of this invention can vary depending upon the number of replaceable hydrogen atoms on the electron rich aromatic ring. For example, in the case of diphenylamine substituted only on one ring by a single branched chain alkyl group containing in the range of 3 to about 24 carbon atoms, the number of unsubstituted positions is nine while the number of activated positions in most cases is actually five, and thus the number of 2,6-dihydrocarbyl-4-hydroxybenzyl groups on the diphenylamine rings of a product of this invention will typically be no greater than five.

In some embodiments, the macromolecular antioxidant products of the present invention can be, and preferably are, characterized as having one or more, preferably two or more, more preferably all of the following properties:
1. substantially free of unreacted aromatic amine starting material
2. substantially free of the phenolic starting material
3. substantially free of aromatic amines substituted with one 3,5-di-hydrocarbyl-4-hydroxylbenzyl groups
4. have very low levels of aromatic amines substituted with two 3,5-di-hydrocarbyl-4-hydroxylbenzyl groups, by very low it is meant within the ranges described above
5. are rich in poly-substituted aromatic amines, by rich it is meant within the ranges described above 6. contain alkylated methylene-bridged amine phenolic macromolecules.

In preferred embodiments, if the reaction products of the present invention are described as having one of 1-6, it is 6.

The macromolecular antioxidant compositions of the present invention can also be described as liquid or low melting amorphous solids with high solubility in engine oils, as described above.

Use of Reaction Products of the Present Invention

The reaction products of the present invention can be made available for use or sale as "neat" compositions for use as an antioxidant in any organic substrate material normally susceptible to oxidative deterioration in the presence of air or oxygen. In this usage, an antioxidant quantity of a novel product of this invention can be blended with the substrate such as, for example, a lubricating oil; a liquid fuel; a thermoplastic polymer, resin or oligomer; or a natural or synthetic rubber or elastomer.

Additive compositions of this invention constitute another way of protecting such organic material against premature oxidative deterioration in the presence of air or oxygen. Thus, when adapted for use as an additive in oils, one or more reaction products of this invention can be partially diluted or dissolved in a base oil or process oil, or can be blended with other components that are commonly used in a wide variety of lubricants. Examples of base oils that may be used include Group I, II, and III mineral oils, poly-alpha-olefins, synthetic esters, gas to liquid derived oils and bio-based oils. Examples of other additives that may be used to produce new and useful lubricant additive blends with the reaction products of the invention include, but are not limited to, dispersants, detergents, anti-wear additives, extreme pressure additives, corrosion inhibitors, rust inhibitors, friction modifiers, pour point depressants, viscosity index modifiers, emulsifiers, demulsifiers, seal swell agents, solubilizing agents, antifoam agents, acid scavengers, metal deactivators, and other antioxidants or stabilizers. Combinations of one or more of these components can be used to produce additive blends with one or more of the reaction products of this invention. Also, additive compositions for use in internal combustion engine oils, railroad and marine lubricants, natural gas engine oils, gas turbine oils, steam turbine oils, aviation turbine oils, rust and oxidation oils, hydraulic fluids, compressor fluids, slideway oils, quench oils, manual and automatic transmission fluids, gear oils, greases, etc. can be formed by blending one or more of the reaction products of this invention with a diluent, solvent, or carrier fluid and/or one or more other suitable additives. The additive compositions of this invention adapted for use in oils can contain in the range of 5 wt % to 95 wt % depending upon the number and type of other components in the blend, based on the total weight of the additive composition. Finished lubricating oils of this invention will contain an antioxidant quantity of a product of this invention, which amount typically is at least about 0.1 wt %, preferably at least about 1 wt %, and more preferably at least about 3 wt %, based on the total weight of the finished lubricating oil. Depending upon the type of service for which the oil of lubricating viscosity is intended, the amount of the product of this invention blended therein either as a sole additive or as an additive composition containing one or more other components will typically be no more than about 15 wt %, on the same basis.

The lubricating oil used in these embodiments of the present invention can be mineral, synthetic, or a blend of mineral and/or synthetic lubricating oils. These oils are typical industrial or crankcase lubrication oils for gas or steam turbines, transmission or hydraulic fluids, spark-ignited and compression-ignited internal combustion engines, for example natural gas engines, automobile and truck engines, marine, and railroad diesel engines. Mineral lubricating oils can be refined from aromatic, asphaltic, naphthenic, paraffinic or mixed base crudes. The lubricating oils can be distillate or residual lubricating oils, such as for example, bright stock, or blends of the oils to give a finished base stock of desired properties. Synthetic base oils used can be (i) alkyl esters of dicarboxylic acids, polyglycols and alcohols, (ii) poly-alpha-olefins, including polybutenes, (iii) alkyl benzenes, (iv) organic esters of phosphoric acids, or (v) polysilicone oils. The base oil typically has a viscosity of about 2 to about 15 cSt and preferably about 2.5 to about 11 cSt at 100° C.

Additive compositions adapted for use in forming liquid fuel compositions of this invention (e.g., gasolines, diesel fuels, jet fuels, gas turbine engine fuels, etc.) can be formed by blending therewith or providing therein an antioxidant quantity of one or more of the reaction products of this invention in the form of an additive composition of this invention comprising at least one novel compound of this invention together with one or more other additives, such as detergents, carrier fluids, demulsifiers, corrosion inhibitors, metal deactivators, lubricity agents, pour point depressants, cetane or octane improvers, antiknock agents, anti-icing agents, etc. The substrate fuels can be derived from petroleum or can be synthetic fuels, or they can be blends of both such types of materials. The amount of these new compositions in an additive blend of this invention can vary from 5 wt % to 95 wt %, based on the total weight of the additive blend, depending on the type and number of other components in the blend.

Liquid fuel compositions of this invention are typically formed by blending an antioxidant quantity of at least one of the reaction products of this invention with the fuel, either as a single additive composition (i.e., containing no other type(s) of fuel additive) or as an additive concentrate comprised of at least one of the reaction products of this invention together with at least one other type of fuel additive. The additive concentrates of this invention thus can contain in the range of about 5 to about 95 wt % of at least one of the reaction products of this invention, with the balance to 100 wt % being one or more other additives and optionally, a diluent, solvent or carrier fluid, all based on the total weight of the additive concentrate. The finished fuel compositions typically contain an antioxidant quantity in the range of about 0.0001 to about 0.1 wt %, and preferably in the range of about 0.001 to about 0.05 wt % of at least one of the reaction products of this invention, all based on the total weight of the finished fuel composition.

It will of course be understood that on blending one or more of the reaction products of this invention with a liquid substrate fuel or oil, the reaction products of this invention may no longer exist in exactly the same composition and form as they were upon addition to such substrate fuel or oil. For example, they may interact with one or more of the other components in the fuel or oil and/or they may complex with or otherwise change by virtue of becoming dissolved in the substrate fuel or oil. However, since the finished fuel or lubricant possess antioxidant properties because of the addition thereto of the one or more reaction products of this invention, the possibility of such transformations upon dilution in the substrate matters not. What matters pursuant to this invention is that whatever is formed upon such dilution is effective as an antioxidant. Consequently, expressions such as "containing in the range of", "in", etc. with reference to at least one of the reaction products of this invention are to be understood as referring to the at least one of the reaction products of this invention as it existed just prior to being blended or mixed with any liquid fuel or base oil and/or with any other component.

It will also be understood that the amount of the reaction products of this invention in a finished lubricant will vary depending upon the lubricant type, the identity of the one or more reaction products of this invention being used, and the desired level of performance required. For example, in a turbine oil, levels of the reaction product(s) of this invention often vary from about 0.05 to about 1.0 wt %, based on the total weight of the finished turbine oil. However, in an engine oil, levels typically vary from about 0.2 to about 2 wt %, based on the total weight of the engine oil. In low phosphorus engine oils, levels may vary from about 0.3 to about 3 wt %, based on the total weight of the low phosphorus engine oil. In phosphorus-free engine oils levels may be as high as about 4 or 5 wt %, based on the total weight of the phosphorus-free engine oil. It will be understood that all wt. % are based on the total weight of the finished oil containing all additives, etc. When used properly the reaction products of this invention serve as antioxidant compositions. Thus, this invention also provides novel improved methods of reducing oxidation, reducing viscosity increase and polymerization, reducing acid formation and retaining lubricant basicity (TAN and TBN), reducing varnish and deposit formation, reducing friction and wear, reducing dependence on ZDDP and phosphorus for oxidation and deposit control, extending the usable life of all lubricant mentioned above, and reducing oil changes and vehicle maintenance. In each of such methods, a lubricant composition of this invention comprising an oil of lubricating viscosity with which has been blended an antioxidant quantity of at least one novel product of this invention is utilized as the lubricant. Still another method of this invention is a method of improving the oxidation stability of a lubricating oil, wherein said method comprises blending with a lubricating oil an oxidation stability improving amount of at least one reaction product of this invention. In this way the oxidation stability of the oil is significantly improved, as compared to the same oil devoid of a reaction product of this invention.

An example of an engine oil composition of this invention is formed by blending together components that comprise:

Detergent: 0.5 to 5.0 wt % as pure component or concentrate. Concentrates typically contain 25 to 90 wt % diluent oil;

Dispersant: 1.0 to 10.0 wt % as pure component or concentrate. Concentrates typically contain 25 to 90 wt % diluent oil;

Zinc dialkyldithiophosphate (ZDDP): 0.1 to 1.5 wt % as pure component (with the lower amounts being preferred);

Viscosity Modifier as an optional component: 1.0 to 15.0 wt % as pure component or concentrate. Concentrates typically contain 5 to 50 wt % diluent oil;

Additional antioxidant(s) as one or more additional optional components: 0.01 to 1.0 wt % as pure component or concentrate. Concentrates typically contain 25 to 90 wt % diluent oil;

Additional additives as one or more optional components used in amounts sufficient to provide the intended function of the additive(s): one or more friction modifiers, supplemental anti-wear additives, anti-foam agents, seal swell agents, emulsifiers, demulsifiers, extreme pressure additives, corrosion inhibitors, acid scavengers, metal deactivators, and/or rust inhibitors;

At least one product of this invention: 0.1-2.5 wt %; with the balance to 100 wt % composed of one or more base oils.

It will be understood that all wt. % are based on the total weight of the finished oil containing all additives, etc.

Also provided by this invention are novel compositions comprised of at least one reaction product of this invention combined with:
1) at least one conventional hindered phenolic antioxidant
2) at least one conventional alkylated diphenylamine antioxidant
3) at least one organomolybdenum compound
4) at least one alkylated diphenylamine and at least one organomolybdenum compound
5) at least one phosphorus-free anti-wear or extreme pressure additive
6) at least one molybdenum-containing or boron-containing dispersant
7) at least one organoboron compound
8) at least one organoboron compound and at least one conventional alkylated diphenylamine
9) at least one sulfurized antioxidant, EP (extreme pressure) additive or anti-wear additive
10) at least one conventional alkylated diphenylamine along with at least one (i) sulfurized antioxidant, (ii) EP additive, (iii) anti-wear additive, and (iv) organoboron compound.
11) at least one base oil or process oil.

It will be understood, that it is within the scope of the present invention, that the compositions described in this paragraph can contain any one of 1)-11) or combinations of any two or more of 1)-11).

Processes for Forming the Products of the Invention

The macromolecular reaction products of the present invention can be formed by, for example, using as reactants:
(A) a sterically hindered 4-alkoxymethyl-2,6-dihydrocarbylphenol, preferably a sterically hindered 4-alkoxymethyl-2,6-dialkylphenol and more preferably, a 4-alkoxymethyl-2,6-di-tert-butylphenol in which the alkoxymethyl group is ethoxymethyl or methoxymethyl, and still more preferably, 4-methoxymethyl-2,6-di-tert-butylphenol; or a sterically hindered 4-hydroxymethyl-2,6-dihydrocarbylphenol, preferably a sterically hindered 4-hydroxymethyl-2,6-dialkylphenol, and more preferably a 4-hydroxymethyl-2,6-di-tert-butylphenol and
(B) at least one aromatic amine having in the range of 1 to about 4 aromatic rings in the molecule which rings are in the form of fused rings or singly bonded rings, or both, and having at least one primary amino group ($-NH_2$), secondary amino group (—NHR where R is a hydrocarbyl group containing up to about 18 carbon atoms), or tertiary amino group ($NR_2$ where each R is independently a hydrocarbyl group containing up to about 18 carbon atoms), and preferably at least one such primary or secondary amino group; or
wherein (B) (a) has at least one replaceable hydrogen atom on a ring thereof, (b) is substituted by one or more branched chain alkyl groups each having in the range of 3 to about 24 carbon atoms and preferably, in the range of 4 to about 12 carbon atoms, and (c) optionally, has one or more additional alkyl side chains each having in the range of 1 to about 3 carbon atoms.

In such processes, reactant (A) is combined with reactant (B) in the presence of (C) an alkylation catalyst, and optionally (D) an organic solvent, thus forming a reaction product that is suitable as, among other things, an antioxidant.

Component (A)

The sterically hindered 4-alkoxymethyl-2,6-dihydrocarbylphenol or 4-hydroxymethyl-2,6-dihydrocarbylphenol, used as a reactant in the processes of this invention can be any of a relatively large group of compounds. The hydrocarbyl groups in the ortho positions relative to the carbon atom carrying the hydroxyl group can be any univalent hydrocarbon group with the proviso that the resultant substitution in the 2- and 6-positions provides steric hindrance to the hydroxyl group. Typically, a total of at least 4 or 5 carbon atoms in the ortho positions is required to achieve steric hindrance. Among suitable hydrocarbyl groups that can be in the ortho positions are alkyl, cycloalkyl, alkenyl, cycloalkenyl, cycloalkylalkyl, aryl, and aralkyl in which the cyclic moieties, whether saturated or unsaturated, can in turn be alkyl substituted. The alkyl and alkenyl groups can be linear or branched. The individual hydrocarbyl groups in the ortho positions can each contain in the range of 1 to about 12 carbon atoms with the total number of carbon atoms in the ortho positions being in the range of about 4 to about 18 carbon atoms and preferably in the range of 8 to about 16 carbon atoms. 4-Alkoxymethylphenols or 4-hydroxymethylphenols in which at least one of the ortho positions is substituted by a tertiary alkyl group are preferred. The alkoxy group can be linear or branched and can contain up to about 18 carbon atoms and preferably up to about 6 carbon atoms. Preferred are the 4-alkoxymethyl hindered phenols in which the alkoxy group is ethoxy, and more preferably where the alkoxy group is methoxy. Branching of alkyl or alkenyl groups can occur anywhere in the alkyl or alkenyl group, including on the alpha-carbon atom of a secondary alkyl group such as isopropyl or sec-butyl, or on more remote positions such as on the beta-position in 2-ethylhexyl. Also, there can be any number of branches in the alkyl or alkenyl group, such as, for example, the four branches in a 1,1,3,3-tetramethylbutyl group.

Non-limiting examples of suitable sterically hindered 4-alkoxymethyl-2,6-dihydrocarbylphenols include, 4-ethoxymethyl-2,6-diisopropylphenol, 4-methoxymethyl-2-tert-butyl-6-methylphenol, 4-butoxymethyl-2,6-di-tert-butylphenol, 4-hexadecyloxymethyl-2-tert-butyl-6-methylphenol, 4-decyloxymethyl-2-tert-butyl-6-isopropylphenol, 4-hexyloxymethyl-2-cyclohexyl-6-ethylphenol, 4-methoxymethyl-2-tert-butyl-6-phenylphenol, 4-propoxymethyl-2-benzyl-6-isopropylphenol, 4-ethoxymethyl-2,6-di-tert-butylphenol, 4-methoxymethyl-2,6-di-tert-butylphenol, 4-(2-ethylhexyloxymethyl)-2,6-di-tert-butylphenol, and analogous hindered phenolic compounds. A preferred sub-group of sterically hindered 4-alkoxymethyl-2,6-dialkylphenols are those in which one of the ortho alkyl groups is tert-butyl and the other is methyl or, more preferably, tert-butyl and in which the alkoxymethyl group has a total of 9 carbon atoms. Particularly preferred is 4-methoxymethyl-2-tert-butyl-6-methylphenol. More especially preferred is 4-methoxymethyl-2,6-di-tert-butylphenol.

Non-limiting examples of suitable sterically hindered 4-hydroxymethyl-2,6-dihydrocarbylphenols include, 4-hydroxymethyl-2,6-diisopropylphenol, 4-hydroxymethyl-2-tert-butyl-6-methylphenol, 4-hydroxymethyl-2,6-di-tert-butylphenol, 4-hydroxymethyl-2-tert-butyl-6-methylphenol, 4-hydroxymethyl-2-tert-butyl-6-isopropylphenol, 4-hydroxymethyl-2-cyclohexyl-6-ethylphenol, 4-hydroxymethyl-2-tert-butyl-6-phenylphenol, 4-hydroxymethyl-2-benzyl-6-isopropylphenol, 4-hydroxymethyl-2,6-di-tert-butylphenol, and analogous hindered phenolic compounds. A preferred sub-group of sterically hindered 4-hydroxymethyl-2,6-dialkylphenols are those in which one of the ortho alkyl groups is tert-butyl and the other is methyl or, more preferably, tert-butyl. Particularly preferred is 4-hydroxymethyl-2-tert-butyl-6-methylphenol. In one exemplary embodiment, (A) is 4-hydroxymethyl-2,6-di-tert-butylphenol.

Component (B)

In the practice of the present invention, a broad range of aromatic amines are contemplated for use in the present invention. The aryl groups can have one, two or more rings, e.g., they can be phenyl, naphthyl, etc., and can be substituted or unsubstituted. Each aryl group can have in the range of 6 to 36 or more carbon atoms depending upon the nature and degree of substitution although generally they will have from 6 to about 18 carbon atoms. Substituted diphenylamines wherein at least one of the rings is substituted by a branched chain alkyl group having in the range of 3 to about 24 and preferably in the range of 4 to about 12 carbon atoms illustrate substitution of this type.

Non-limiting examples of suitable aromatic amines include diphenylamine, one or a mixture of nonylated diphenylamines prepared from, for example, propylene trimer and diphenylamine, one or a mixture of octylated diphenylamines prepared from diisobutylene and diphenylamine, one or a mixture of butylated diphenylamines prepared from isobutylene and diphenylamine, one or a mixture of styrenated diphenylamines prepared from styrene and diphenylamine, phenyl-α-naphthylamine, one or a mixture of nonylated phenyl-α-naphthylamines prepared from propylene trimer and phenyl-α-naphthylamine, one or a mixture of octylated phenyl-α-naphthylamines prepared from diisobutylene and phenyl-α-naphthylamine, one or a mixture of butylated phenyl-α-naphthylamines prepared from isobutylene and phenyl-α-naphthylamine, one or a mixture of styrenated phenyl-α-naphthylamines prepared from styrene and phenyl-α-naphthylamine, ortho-phenylenediamine, para-phenylenediamine, N,N-di-sec-butyl-p-phenylenediamine, aniline, N-methylaniline, N,N-dimethylaniline, toluidine, N-methyl-o-toluidine, N-methyl-p-toluidine, N,N-dimethyl-o-toluidine, N,N-dimethyl-p-toluidine, 2,6-diethylaniline, 2-ethyl-6-methylaniline, 2,6-diisopropylaniline, o-tert-butylaniline, triphenylamine, 2-4'-diaminobiphenyl, 4,4'-diaminobiphenyl, 1-naphthylamine, 2-naphthylamine, N-methyl-1-naphthylamine, N,N-dimethyl-1-naphthylamine, 2-aminobiphenyl, 3-aminobiphenyl, 4-amino-4'-methylbiphenyl and similar alkyl substituted or unsubstituted monoamines or polyamines, and mixtures of any two or more of the foregoing. In some embodiments, (B) is diphenylamine, and in other embodiments, (B) is one or more alkylated diphenylamines.

Component (C)

In the practice of the present invention, an alkylation catalyst is used to promote the reaction between (A) and (B), thus the reaction between (A) and (B) is sometimes referred to as an alkylation reaction herein. The alkylation reaction catalyst used herein can be selected from any alkylation catalyst known to promote the reaction of (A) and (B). In some embodiments, (C) is preferably an acidic catalyst such as sulfuric acid, an aryl sulfonic acid, an alkyl sulfonic acid, or an aryl alkyl sulfonic acid. Non-limiting examples of other suitable alkylation catalysts include, for example, hydrochloric acid, hydrobromic acid, aluminum chloride, diethyl aluminum chloride, triethylaluminum/hydrogen chloride, ferric chloride, zinc chloride, antimony trichloride, stannic chloride, boron trifluoride, acidic zeolites, acidic clays, and polymeric sulfonic acids such as those sold under the name Amberlyst®.

Component (D)

The processes are carried out in a liquid reaction medium that can result from one of the reactants being a liquid under the conditions of the alkylation reaction, or which can result from use of an inert organic solvent. Non-limiting examples of organic solvents which can be used include, for example, acetic acid, propionic acid, one or more hexane isomers, one or more heptane isomers, one or more octane isomers, one or more decanes, mixtures of one or more of the alkane solvents such as the foregoing, cyclohexane, methylcyclohexane, methylene dichloride, methylene di bromide, bromochloromethane, 1,2-dichloroethane, 1,2-dibromoethane, chloroform, chlorobenzene, mixtures of one or more chlorinated and/or brominated solvents such as the foregoing, and one or a mixture of alkanols such as methyl alcohol, ethyl alcohol, isopropyl alcohol, n-propyl alcohol, n-butyl alcohol, sec-butyl alcohol, isobutyl alcohol, 2-ethylhexyl alcohol, octyl alcohol, and other liquid or low melting homologous alkanols, and one or more ethers like dialkyl ethers, tetrahydrofuran, dioxane or mixtures thereof. In some embodiments, the solvent is a hydrocarbon solvent. In preferred embodiments, (D) is used in the practice of the present invention.

Process Conditions

The processes used to product the macromolecular reaction products of the present invention are typically conducted at one or more temperatures in the range of from about 20° C. to about 160° C. or higher. In some embodiments, the processes are conducted at one or more temperatures above 40° C., preferably in the range of from 70° C. to about 160° C., or higher. The inventors hereof have discovered that reaction temperatures within these ranges are more suitable for producing the reaction products of the present invention. Further, the inventors hereof have discovered that at higher temperatures, i.e. greater than 40° C., the processes proceed more rapidly and thus completion can be reached in shorter periods of time than previously contemplated. For example, when 2,6-di-tert-butyl-4-methoxymethylphenol is used as (A), the reaction tends to initiate relatively rapidly at room temperature, (about 23° C.) until about one equivalent of the 2,6-di-tert-butyl-4-methoxymethylphenol has been consumed. Thereafter, the reaction tends to proceed more slowly and consequently additional heat energy needs to be applied and/or additional catalyst employed. However, at higher temperatures, i.e. greater than 40° C., this reaction proceeds more rapidly and thus completion can be reached in shorter periods of time.

With lower boiling reactants and/or solvents the reaction may be conducted under pressure, or the reaction may be conducted in the presence of a cooling condenser. In most cases, the reaction results in alkylation on an activated, electron rich ring. In some cases, alkylation may occur on a nitrogen atom.

The inventors hereof have discovered that by varying the relative molar ratio of (A) to (B), one can produce various macromolecular reaction products, as described below, that find use as antioxidants. In some embodiments, (A) and (B) are used in a molar ratio of (B) to (A) in the range of from about 1:1 to about 1:10, preferably in the range of from about 1:1 to about 1:7; in some embodiments, in the range of from about 1:3 to about 1:10, preferably in the range of from about 1:3 to about 1:7. In preferred embodiments, the molar ratio of (B) to (A) can be any of about 1:1, about 1:2, about 1:2.5, about 1:3, about 1:3.5, about 1:4, about 1:4.5, about 1:5, about 1:5.5, about 1:6, about 1:6.5, or about 1:7.

The above description is directed to several embodiments of the present invention. Those skilled in the art will recognize that other means, which are equally effective, could be devised for carrying out the spirit of this invention. It should also be noted that preferred embodiments of the present invention contemplate that all ranges discussed herein include ranges from any lower amount to any higher amount.

The following examples will illustrate the present invention, but are not meant to be limiting in any manner.

EXAMPLES

Example 1

In this operation, a branched chain nonyldiphenylamine (NDPA) mixture relatively rich in monoalkylated diphenylamine was used as one of the reactants. The composition of this NDPA as shown by GC analysis (area %) was as follows: free DPA, 1.50; ortho-monoalkylated DPA, 0.33; para-monoalkylated DPA, 21.90; ortho-dialkylated DPA, 3.29; para-dialkylated DPA, 65.54, and trialkylated DPA, 7.33, with the alkyl groups being predominately branched chain nonyl groups. The other reactant used was 2,6-di-tert-butyl-4-methoxymethylphenol. Thus, into a 500 mL round-bottomed flask was charged 25.1 g of the branched chain nonyldiphenylamine, 4.0 g of 2,6-di-tert-butyl-4-methoxymethylphenol, 80 g of methylene chloride, 108 g of acetic acid, and 1.6 g of concentrated sulfuric acid catalyst. The mixture was heated at 60° C. for 1 hour and then diluted with 100 g of ether and 100 g of water. After phase separation, the organic phase was washed with water (3×200 g) and dried over $MgSO_4$. The solvent was removed under reduced pressure to obtain 25.3 g of dark thick oil, constituting a product of this invention.

The antioxidant effectiveness of this product of the invention was shown by use of a standardized oxidation test procedure (ASTM D 6186) in which a lubricating oil containing a specified amount of an additive is subjected to oxidation in a heated pressure-resistant vessel at a temperature of 160° C. charged with oxygen under an initial elevated pressure of 500 psig. The longer the induction time (OIT) before a pressure drop occurs, the more stable is the composition.

In one such test a sample of the alkylated NDPA formed in Example 1 was used as the antioxidant. It was blended with EHC 60 oil (a mineral base oil having a kinematic viscosity at 100° C. of 6.1 cSt, a viscosity index of 114, and a Noack volatility of 8 wt %; ExxonMobil) and the resultant blend was subjected to the above oxidation test procedure. For comparative purposes, runs were also conducted wherein NDPA alone was blended with another portion of the same base oil and wherein 2,6-di-tert-butyl-4-methoxymethylphenol alone was blended with another portion of the same base oil. The results of these tests are summarized in Table 1.

TABLE 1

Antioxidant Effectiveness of Additives in a Lubricating Oil at 160° C. and Under 500 psig Oxygen Pressure

| Additive | OIT at 0.5 wt % (minutes) | OIT at 0.75 wt % (minutes) |
| --- | --- | --- |
| NDPA only | 107 | 124 |
| 2,6-Di-tert-butyl-4-methoxymethylphenol | 80 | 100 |
| Product of this invention (Ex. 1) | 135 | 157 |
| OIT Difference Over NDPA | 28 | 33 |
| Percent Effectiveness Over NDPA | 26% | 27% |

Example 2

A three-necked round-bottomed flask was equipped with an addition funnel, magnetic stirrer, temperature probe, and a condenser. Diphenylamine (0.02 mol, 3.4 g) was dissolved in dichloromenthane (20 mL) and sulfuric acid (10 mL of 80%) was added at room temperature. A solution of 2,6-di-tert-butyl-4-methoxymethylphenol (0.12 mol, 30 g) in dichloromethane (60 mL) was added at room temperature and in small increments (about 2 mL/minute)). An exothermic reaction ensued during the addition of the first equivalent of 2,6-di-tert-butyl-4-methoxymethylphenol, but it subsided when the addition continued. The reaction mixture was brought to 40-45° C. and addition of the 2,6-di-tert-butyl-4-methoxymethylphenol was completed in 5 hrs. The reaction mixture was stirred at room temperature overnight. The acid phase was separated and the organic phase was washed with water (2×30 mL), dilute sodium hydroxide to a pH of 7-8, water (1×30 mL), and dried over magnesium sulfate. Evaporation of solvent under water aspirator pressure afforded bright yellow/orange solid. Analysis by NMR and LC-Mass showed 4,4'-methylenebis(2,6-di-tert-butylphenol) (14%), penta-substituted isomer (5%), hexa-substituted isomer (30%), and higher molecular weight components (51%). Oxidation Inhibition Time measured by PDSC was 99 minutes at 0.25%, 123 minutes at 0.50%, and 136 minutes at 0.75% loading.

Example 3

A three-necked round-bottomed flask was equipped with an addition funnel, magnetic stirrer, temperature probe, and a condenser. Diphenylamine (0.1 mol, 16.9 g) was dissolved in dichloromenthane (40 mL) and sulfuric acid (10 mL of 80%) was added at room temperature. A solution of 2,6-di-tert-butyl-4-methoxymethylphenol (0.3 mol, 75 g) in dichloromethane (130 mL) was added at room temperature and in small increments. An exothermic reaction ensued during the addition of the first equivalent of 2,6-di-tert-butyl-4-methoxymethylphenol, but it subsided when the addition continued. The reaction mixture was brought to 40-45° C. and addition of the 2,6-di-tert-butyl-4-methoxymethylphenol was completed in 3 hrs. The reaction mixture was stirred at room temperature overnight. The acid phase was separated and the organic phase was washed with water (2×30 mL), dilute sodium hydroxide to a pH of 7-8, and water (1×30 mL) and dried over magnesium sulfate. Evaporation of solvent under water aspirator pressure afforded bright yellow/orange solid. Analysis by NMR and LC-Mass showed mono-substituted isomer (6%), di-substituted isomer (26%), tri-substituted isomer (29%), tetra-substituted isomer (28%), penta-substituted isomer (5%). Oxidation Inhibition Time (OIT) measured by PDSC was 138 minutes at 0.25%, 170 minutes at 0.50%, and 191 minutes at 0.75% loading.

Example 4

A four-necked flask was equipped with mechanical stirrer, addition funnel, condenser, nitrogen inlet, and a temperature probe. Diphenylamine (38.9 g), toluene (175 mL), concentrated sulfuric acid (3 g, 98%), and acetic acid (6 g) were charged into the reactor. The stirred reaction mixture was heated to about 70° C. and a warm solution of 2,6-di-tert-butyl-4-methoxymethylphenol (300 g) in toluene (350 mL) was charged over a two hours period at about 70° C. and the methanol co-product was distilled overhead. The reaction was complete after a total of 6 hours at these conditions. The reaction mixture was washed with water (2×200 mL). Toluene was removed by distillation and the resulting oily residue was heat treated (60-80° C. and 2-10 mmHg) for 1 hour. The resulting oily product solidified on standing at room temperature. Analysis by HPLC showed zero percent mono-substituted, zero percent di-substituted, 1% tri-substituted, 14% tetra-substituted, 43% penta-substituted, 24% hexa-substituted diphenylamine products. In addition 3.4 wt % of 4,4'-methylenebis(2,6-di-tert-butylphenol) and 15% of methylene-bridged products and other oligomeric materials were identified in the sample.

Example 5

The same procedure as Example 3 was used, except a diphenylamine/2,6-di-tert-butyl-4-methoxymethylphenol mole ratio of 1:3 was used. The product contained 1% mono-substituted, 17% di-substituted, 36% tri-substituted, 22% tetra-substituted, 2% penta-substituted, 1% hexa-substituted diphenylamine products. In addition 4.3 wt % of 4,4'-methylenebis(2,6-di-tert-butylphenol) and 15% of methylene-bridged products and other oligomeric materials were identified in the sample.

Example 6

The same procedure as Example 3 was used, except a diphenylamine/2,6-di-tert-butyl-4-methoxymethylphenol mole ratio of 1:4 was used. The product contained 1% mono-substituted, 1% di-substituted, 14% tri-substituted, 34% tetra-substituted, 11% penta-substituted, 1% hexa-substituted diphenylamine products. In addition 6.0 wt % of 4,4'-methylenebis(2,6-di-tert-butylphenol) and 26% of methylene-bridged products and other oligomeric materials were identified in the sample.

Example 7

The same procedure of example 5 was attempted but the sulfuric acid used was replaced with methanesulfonic acid. The product contained 1% mono-substituted, 2% di-substituted, 13% tri-substituted, 40% tetra-substituted, 23% penta-substituted, 3% hexa-substituted diphenylamine products. In addition 4.7 wt % of 4,4'-methylenebis(2,6-di-tert-butylphenol) and 13% of methylene-bridged products and other oligomeric materials were identified in the sample.

Example 8

The procedure of example 3 was attempted but toluene was replaced with methanol and sulfuric acid with Amberlyst® 35 catalyst. The product contained 0.5% mono-substituted, 3% di-substituted, 19% tri-substituted, 56% tetra-substituted, 15% penta-substituted, 0.5% hexa-substituted diphenylamine products. In addition 1.7 wt % of 4,4'-methylenebis (2,6-di-tert-butylphenol) and 4% of methylene-bridged products and other oligomeric materials were identified in the sample.

Example 9

Diphenylamine ("DPA") and 2,6-di-tert-butyl-4-methoxymethylphenol ("Phenol") were used to produce several antioxidant compositions according to the present invention. The molar ratio of the components and conditions used along with the contents of the antioxidant product thus formed are contained in Table 1, below.

TABLE 1

| Product | DPA/phenol | Solvent | Temp., °C. | Mono- | Di- | Tri- | Tetra- | Penta- | Hexa- | Others |
|---|---|---|---|---|---|---|---|---|---|---|
| Antioxidant-1 | 1/3.5 | Toluene | 70 | 0.5 | 4 | 26 | 47 | 12 | 0.5 | 7 |
| Antioxidant-2 | 1/3.5 | Toluene | 130 | 0.1 | 9 | 24 | 31 | 9 | 0.1 | 22 |
| Antioxidant-3 | 1/4.0 | Toluene | 70 | 0.5 | 0.5 | 5 | 39 | 38 | 6 | 10 |
| Antioxidant-4 | 1/4.0 | Toluene | 130 | 0.1 | 4 | 14 | 33 | 14 | 4 | 25 |
| Antioxidant-5 | 1/4.25 | Methanol | 110 | 0.5 | 3 | 17 | 46 | 15 | 2 | 12 |

All the products identified in Table 1 contained between 2-3.5 wt % of 4,4'-methylenebis(2,6-di-tert-butylphenol).

Comparative Example 1

The process described in U.S. Pat. No. 3,673,091 was repeated. The product was analyzed by LC-Mass and contained 35% unreacted diphenylamine, 43% mono-substituted, 16% disubstituted, and 2% tri-substituted product with less than 1% of higher substituted isomers. The components of the antioxidant product thus produced, and their amounts, are illustrated in Table 2, below.

Comparative Example 2

The process described in U.S. Pat. No. 3,673,091 was repeated with a diphenylamine and 2,6-di-tert-butyl-4-hydroxybenzylalcohol mole ratio of 1:4. The isolated product contained 20% mono-substituted, 36% di-substituted, 21% tri-substituted, 3% tetra-substituted, less than 0.5% penta-substituted, less than 0.1% hexa-substituted isomers and no methylene-bridged oligomers. The components of the antioxidant product thus produced, and their amounts, are illustrated in Table 2, below.

Comparative Example 3

Diphenylamine and 2,6-di-tert-butyl-4-hydroxybenzylalcohol ("Alcohol") were reacted according to the process of Example 2 using varying mole ratios, the mole ratios and reaction times are indicated in Table 2. The components of the antioxidant product thus produced, and their amounts, are illustrated in Table 2, below.

hydrocarbyl-4-hydroxylbenzyl groups; ii) aromatic amines substituted with two 3,5-di-hydrocarbyl-4-hydroxylbenzyl groups; iii) aromatic amines substituted with three 3,5-di-hydrocarbyl-4-hydroxylbenzyl groups; iv) aromatic amines substituted with four 3,5-di-hydrocarbyl-4-hydroxylbenzyl groups; v) aromatic amines substituted with five 3,5-di-hydrocarbyl-4-hydroxylbenzyl groups; or vi) aromatic amines substituted with six 3,5-di-hydrocarbyl-4-hydroxylbenzyl groups; and (b) one or more methylene-bridged aromatic amines substituted with one or more 3,5-di-hydrocarbyl-4-hydroxylbenzyl groups, wherein the macromolecular antioxidant products are liquid at room temperatures or solids that melt at less than about 100° C. and are capable of being dissolved in liquid hydrocarbon solvents, and wherein said macromolecular antioxidant product contains in the range of from about 1 to about 10 wt. % of one or more phenolics represented by the following general formula:

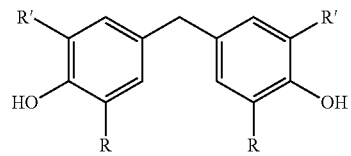

wherein each R and R' are independently H or a hydrocarbyl.

2. A macromolecular reaction product comprising (a) i) less than about 5 wt. % of one or more aromatic amines substituted with one 3,5-di-hydrocarbyl-4-hydroxylbenzyl groups; ii) less than about 10 wt. % of one or more aromatic

TABLE 2

| Experiment | Solvent | Catalyst | RxN Time | DPA/Alcohol | Mono- | Di- | Tri- | Tetra- | Penta- | Hexa- | Others |
|---|---|---|---|---|---|---|---|---|---|---|---|
| U.S. Pat. No. 3,673,091 | acetic acid | Sulfuric | 24 hrs | one/one | 43 | 16 | 2 | <1 | <1 | <1 | 39* |
| U.S. Pat. No. 3,673,091 | acetic acid | sulfuric | 10 hrs | one/four | 20 | 36 | 21 | 3 | <0.5 | <0.1 | <0.5 |
| This invention | Dichloromethane | Sulfuric | 24 hrs | one/four | <0.5 | 4 | 21 | 53 | 18 | <0.5 | 3 |
| This invention | Dichloromethane | Sulfuric | 2 hrs | one/four | 1 | 10 | 18 | 39 | 24 | 4 | 3 |
| This invention | Dichloromethane | Sulfuric | 4 hrs | one/five | <0.5 | <0.5 | 2 | 20 | 47 | 20 | 8 |
| This invention | Dichloromethane | Sulfuric | 6 hrs | one/seven | <0.5 | <0.5 | <0.5 | 3 | 5 | 49 | 28 |

*Unreacted diphenylamine

All products identified in Table 2 contained between 0.1-7.0 wt % of 4,4'-methylenebis(2,6-di-tert-butylphenol).

The novel products of this invention are also effective as antioxidants for use in natural or synthetic rubbers or elastomers, and synthetic polymers especially thermoplastic oligomers, thermoplastic polymers, and thermoplastic resins. Amounts of up to about 10 wt % are usually sufficient to provide inhibition of oxidative deterioration during use or storage of these materials in the presence of air or oxygen.

What is claimed is:

1. A macromolecular antioxidant product comprising (a) one or more i) aromatic amines substituted with one 3,5-diamines substituted with two 3,5-di-hydrocarbyl-4-hydroxylbenzyl groups; iii) in the range of from about 1 wt. % to about 35 wt. % of one or more aromatic amines substituted with three 3,5-di-hydrocarbyl-4-hydroxylbenzyl groups; greater than 40 wt. % of at least one of iv) one or more aromatic amines substituted with four 3,5-di-hydrocarbyl-4-hydroxylbenzyl groups v) one or more aromatic amines substituted with five 3,5-di-hydrocarbyl-4-hydroxylbenzyl groups; vi) one or more aromatic amines substituted with six 3,5-di-hydrocarbyl-4-hydroxylbenzyl groups; and (b) in the range of from about 1 to about 20 wt. % of one or more methylene-bridged aromatic amines substituted with one or more 3,5-dihydrocarbyl-4-hydroxylbenzyl groups, wherein all wt. % are based on the total weight of the macromolecular reaction product, said macromolecular reaction product is liquid at room temperature or solids that melt at less than about 100° C., and said macromolecular reaction product contains in the range of from about 1 to about 10 wt. % of one or more phenolics represented by the following general formula:

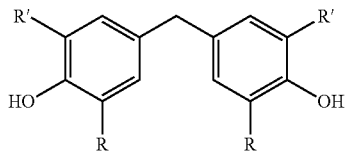

wherein each R and R' are independently H or a hydrocarbyl.

3. The macromolecular reaction product according to claim 2 wherein said macromolecular reaction product comprises (a)
  i) less than about 5 wt. % aromatic amines substituted with one 3,5-di-hydrocarbyl-4-hydroxylbenzyl group, based on the total weight of the macromolecular reaction product;
  ii) less than about 10 wt. % aromatic amines substituted with two 3,5-di-hydrocarbyl-4-hydroxylbenzyl groups, based on the total weight of the macromolecular reaction product;
  iii) in the range of from about 1 wt. % to about 35 wt. % aromatic amines substituted with three 3,5-di-hydrocarbyl-4-hydroxylbenzyl groups, based on the total weight of the macromolecular reaction product;
  iv) in the range of from about 10 wt % to about 65 wt. % aromatic amines substituted with four 3,5-di-hydrocarbyl-4-hydroxylbenzyl groups, based on the total weight of the macromolecular reaction product;
  v) in the range of from about 5 wt % to about 60 wt. % aromatic amines substituted with five 3,5-di-hydrocarbyl-4-hydroxylbenzyl groups, based on the total weight of the macromolecular reaction product;
  vi) in the range of from about 1 wt % to about 50 wt. % aromatic amines substituted with six 3,5-di-hydrocarbyl-4-hydroxylbenzyl groups, based on the total weight of the macromolecular reaction product; and
(b) in the range of from about 1 to about 15 wt. % of one or more methylene-bridged aromatic amines substituted with one or more 3,5-di-hydrocarbyl-4-hydroxylbenzyl groups,
wherein said macromolecular reaction product contains in the range of from about 1 to about 5 wt. % of one or more phenolics represented by the following general formula:

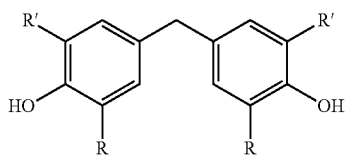

wherein each R and R' are independently H or a hydrocarbyl.

4. The macromolecular reaction product according to claim 2, wherein said macromolecular reaction product contains one or more of the following compounds:

a)

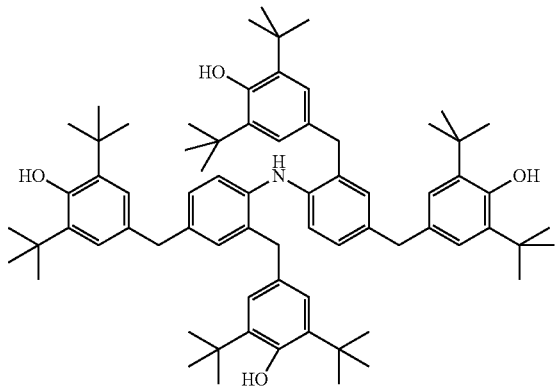

b)

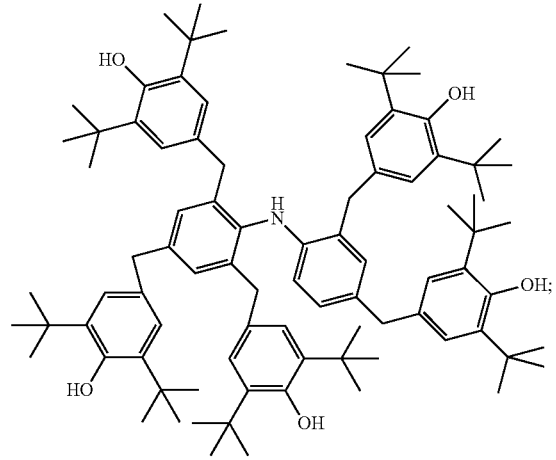

c)

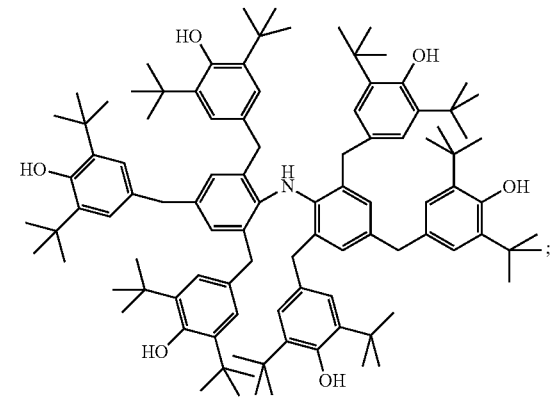

-continued d)

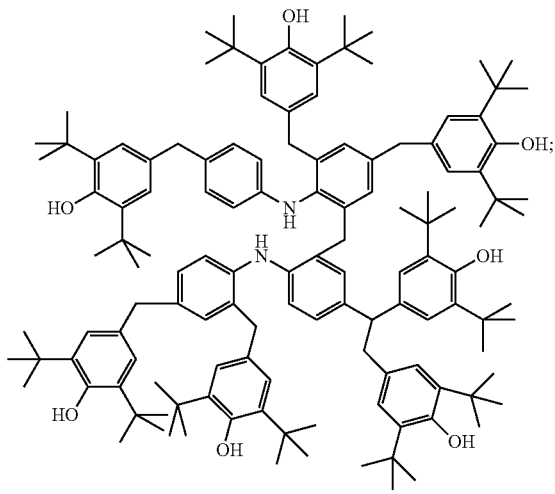

e)

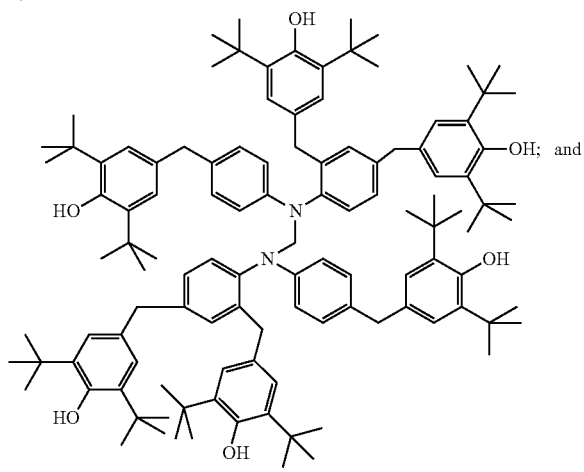

f)

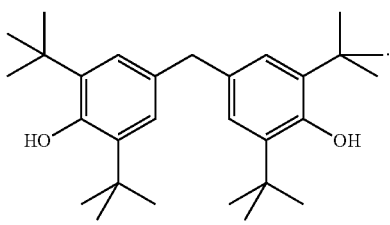

5. A composition comprising:
a) one or more organic materials that are susceptible to oxidation in the presence of air or oxygen selected from at least one oil of lubricating viscosity selected from Group I, II, and III mineral oils, poly-alpha-olefins, synthetic esters, gas to liquid derived oils, bio-based oils, internal combustion engine oils, railroad and marine lubricants, natural gas engine oils, gas turbine oils, steam turbine oils, aviation turbine oils, rust and oxidation oils, hydraulic fluids, compressor fluids, slideway oils, quench oils, manual and automatic transmission fluids, gear oils, and greases;
b) an antioxidant product selected from
 i) Antioxidant Product One, containing:
  (1) less than about 5 wt. % aromatic amines substituted with one 3,5-di-hydrocarbyl-4-hydroxylbenzyl group, based on the total weight of Antioxidant Product One;
  (2) less than about 10 wt. % aromatic amines substituted with two 3,5-di-hydrocarbyl-4-hydroxylbenzyl groups, based on the total weight of Antioxidant Product One;
  (3) in the range of from about 1 wt. % to about 35 wt. % aromatic amines substituted with three 3,5-di-hydrocarbyl-4-hydroxylbenzyl groups, based on the total weight of Antioxidant Product One;
  (4) in the range of from about 10 wt % to about 65 wt. % aromatic amines substituted with four 3,5-di-hydrocarbyl-4-hydroxylbenzyl groups, based on the total weight of Antioxidant Product One;
  (5) in the range of from about 5 wt % to about 60 wt. % aromatic amines substituted with five 3,5-di-hydrocarbyl-4-hydroxylbenzyl groups, based on the total weight of Antioxidant Product One;
  (6) in the range of from about 1 wt % to about 50 wt. % aromatic amines substituted with six 3,5-di-hydrocarbyl-4-hydroxylbenzyl groups, based on the total weight of Antioxidant Product One;
  (7) in the range of from about 1 to about 20 wt. % of one or more methylene-bridged aromatic amines substituted with one or more 3,5-di-hydrocarbyl-4-hydroxylbenzyl groups, based on the total weight of Antioxidant Product One,
   wherein Antioxidant Product One contains in the range of from about 1 to about 10 wt. % of one or more phenolics represented by the following general formula:

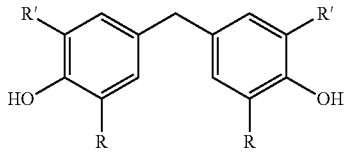

wherein each R and R' are independently H or a hydrocarbyl;
 or
 ii) Antioxidant Product Two, containing
  (1) less than about 1 wt. % aromatic amines substituted with one 3,5-di-hydrocarbyl-4-hydroxylbenzyl group, based on the total weight of Antioxidant Product Two;
  (2) less than about 5 wt. % aromatic amines substituted with two 3,5-di-hydrocarbyl-4-hydroxylbenzyl groups, based on the total weight of Antioxidant Product Two;
  (3) in the range of from about 5 wt. % to about 25 wt. % aromatic amines substituted with three 3,5-di-hydrocarbyl-4-hydroxylbenzyl groups, based on the total weight of Antioxidant Product Two;
  (4) in the range of from about 15 wt % to about 60 wt. % aromatic amines substituted with four 3,5-di-hydrocarbyl-4-hydroxylbenzyl groups, based on the total weight of Antioxidant Product Two;
  (5) in the range of from about 8 wt % to about 50 wt. % aromatic amines substituted with five 3,5-di-hydrocarbyl-4-hydroxylbenzyl groups, based on the total weight of Antioxidant Product Two;
  (6) in the range of from about 5 wt % to about 35 wt. % aromatic amines substituted with six 3,5-di-hydrocarbyl-4-hydroxylbenzyl groups, based on the total weight of Antioxidant Product Two; and (7) in the range of from about 1 to about 20 wt. % of one or more methylene-bridged aromatic amines substituted with one or more 3,5-di-hydrocarbyl-4-hydroxylbenzyl groups, based on the total weight of Antioxidant Product Two, wherein Antioxidant Product Two contains in the range of from about 1 to about 10 wt. % of one or more phenolics represented by the following general formula:

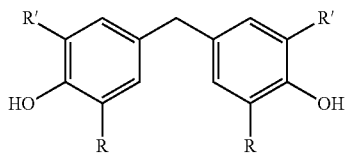

wherein each R and R' are independently H or a hydrocarbyl;

c) one or more additive(s) selected from dispersants, detergents, anti-wear additives, extreme pressure additives, corrosion inhibitors, rust inhibitors, friction modifiers, metal deactivators, lubricity agents, pour point depressants, antiknock agents, anti-icing agents, viscosity index modifiers, emulsifiers, demulsifiers, seal swell agents, solubilizing agents, antifoam agents, other antioxidants or stabilizers, diluents, solvents, carrier fluids, or Zinc dialkyldithiophosphate, at least one hindered phenolic antioxidant, at least one alkylated diphenylamine antioxidant, at least one organomolybdenum compound, at least one alkylated diphenylamine and at least one organomolybdenum compound, at least one phosphorus-free anti-wear or extreme pressure additive, at least one molybdenum-containing or boron-containing dispersant, at least one organoboron compound, at least one organoboron compound and at least one alkylated diphenylamine, at least one sulfurized antioxidant, EP (extreme pressure) additive or anti-wear additive, at least one alkylated diphenylamine along with at least one (i) sulfurized antioxidant, (ii) EP additive, (iii) anti-wear additive, and (iv) organoboron compound.

6. The composition according to claim 5, wherein said antioxidant product contains one or more of the following compounds:

a)

b)

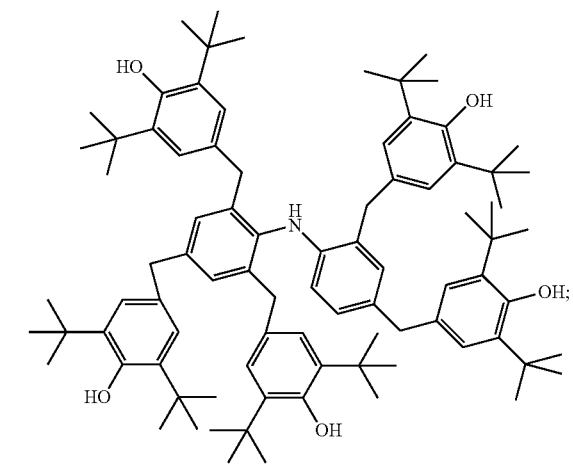

c)

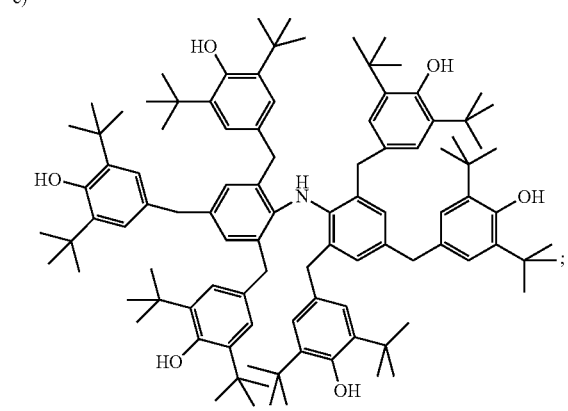

d)

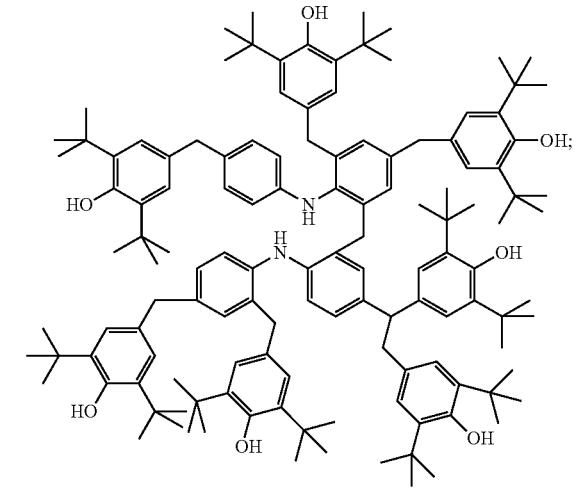

e)

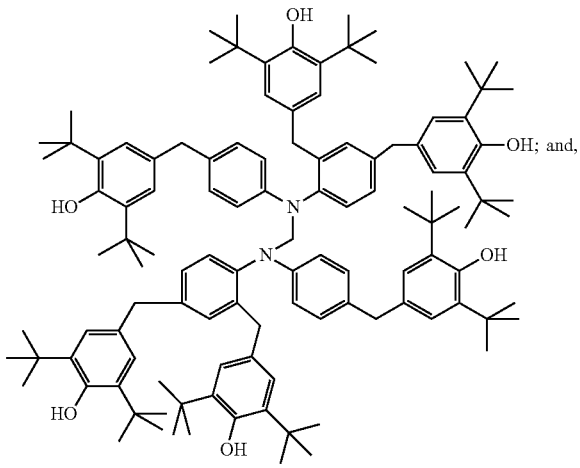

f)

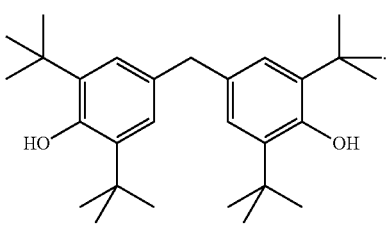

7. The composition according to claim 5 wherein b) and c) are blended with the at least one or more oils as a concentrate, wherein said concentrate contains in the range of from about 5 to about 95 wt. % a) and a diluent oil.

8. The macromolecular reaction product according to claim 2 wherein said macromolecular reaction product comprises (a)

i) less than about 1 wt. % aromatic amines substituted with one 3,5-di-hydrocarbyl-4-hydroxylbenzyl group, based on the total weight of the macromolecular reaction product;

ii) less than about 5 wt. % aromatic amines substituted with two 3,5-di-hydrocarbyl-4-hydroxylbenzyl groups, based on the total weight of the macromolecular reaction product;

iii) in the range of from about 5 wt. % to about 25 wt. % aromatic amines substituted with three 3,5-di-hydrocarbyl-4-hydroxylbenzyl groups, based on the total weight of the macromolecular reaction product;

iv) in the range of from about 15 wt % to about 60 wt. % aromatic amines substituted with four 3,5-di-hydrocarbyl-4-hydroxylbenzyl groups, based on the total weight of the macromolecular reaction product;

v) in the range of from about 8 wt % to about 50 wt. % aromatic amines substituted with five 3,5-di-hydrocarbyl-4-hydroxylbenzyl groups, based on the total weight of the macromolecular reaction product;

vi) in the range of from about 5 wt % to about 35 wt. % aromatic amines substituted with six 3,5-di-hydrocarbyl-4-hydroxylbenzyl groups, based on the total weight of the macromolecular reaction product; and (b) in the range of from about 1 to about 10 wt. % of one or more methylene-bridged aromatic amines substituted with one or more 3,5-di-hydrocarbyl-4-hydroxylbenzyl groups, based on the total weight of the macromolecular reaction product, wherein said macromolecular reaction product contains in the range of from about 1 to about 5 wt. % of one or more phenolics represented by the following general formula:

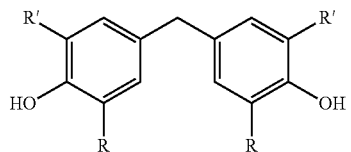

wherein each R and R' are independently H or a hydrocarbyl.

* * * * *

UNITED STATES PATENT AND TRADEMARK OFFICE
CERTIFICATE OF CORRECTION

PATENT NO.       : 8,455,414 B2                                           Page 1 of 1
APPLICATION NO. : 12/444183
DATED            : June 4, 2013
INVENTOR(S)      : Sabahi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1051 days.

Signed and Sealed this
Eighth Day of September, 2015

Michelle K. Lee
*Director of the United States Patent and Trademark Office*